United States Patent [19]

Anderson

[11] Patent Number: 4,774,363

[45] Date of Patent: Sep. 27, 1988

[54] METAL DERIVATIVES OF BUTENEDIOL

[75] Inventor: Lowell R. Anderson, Morristown, N.J.

[73] Assignee: GAF Corporation, Wayne, N.J.

[21] Appl. No.: 109,390

[22] Filed: Oct. 16, 1987

[51] Int. Cl.$^4$ .................. C07C 43/14; C07C 43/15
[52] U.S. Cl. .................. 568/616; 568/675; 568/619; 568/851
[58] Field of Search ............ 568/616, 675, 851, 857, 568/619

[56] References Cited

U.S. PATENT DOCUMENTS

| | | | |
|---|---|---|---|
| 4,048,221 | 9/1977 | Wolf et al. | 260/512 C |
| 4,327,230 | 4/1982 | Ackermann et al. | 568/851 |
| 4,587,365 | 5/1986 | Anchor | 568/619 |

FOREIGN PATENT DOCUMENTS 945152 12/1963 United Kingdom.
946312 1/1964 United Kingdom.

OTHER PUBLICATIONS

Borowiecki et al., Polish Journal of Chemistry, 52, pp. 2173–2180 (1978).

Primary Examiner—Howard T. Mars
Attorney, Agent, or Firm—Marilyn J. Maue; Joshua J. Ward

[57] ABSTRACT

This invention relates to compounds having the structure

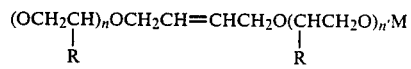

wherein M is an alkali metal and n is an integer having a value of from 0 to 12. The invention also relates to the method of preparing said metal derivatives of butenediol and to their catalytic use in vinylation reactions.

2 Claims, No Drawings

METAL DERIVATIVES OF BUTENEDIOL

In one aspect this invention relates to novel metal derivatives of butenediol and to the preparation of said compounds.

In another aspect the invention relates to the catalytic use of said compounds in the vinylation of alkene diols.

It is an object of this invention to provide novel catalytic materials for use in vinylation reactions to produce the corresponding alkyleneoxylated divinyl ether alkenes by a commercially feasible and economical process.

Another object is to provide a method for the preparation of catalytic metal derivatives of butenediol.

Yet another object of this invention is to provide a continuous method for the preparation of alkylene oxylated divinyl ether alkenes in high yield and purity.

These and other objects of the invention will become apparent from the following description and disclosure.

THE INVENTION

According to this invention there is provided novel compounds having the formula

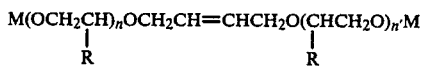   I.

wherein M is an alkali metal, e.g. or sodium, potassium, lithium or cesium; R is hydrogen or methyl and n and n' are integers having a value of from 0 to 12. Of these compounds, those wherein n has a value of from 0 to 4 are preferred and those wherein R is hydrogen and M is sodium or potassium are most preferred.

The present compounds are prepared by the reaction of an alkene diol with a basic alkali metal component, i.e., MOY wherein M is an alkali metal and Y is hydrogen or $C_1$ to $C_4$ alkyl.

The following equation is descriptive of the reaction:

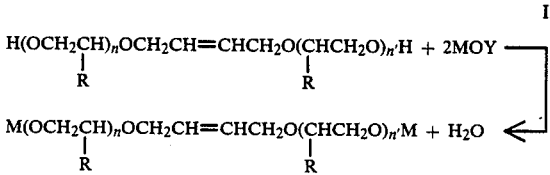   II.

wherein M, R, n and n' are as defined above.

In accordance with this reaction the mole ratio of the diol reactant to alkali metal base is at least 1:1 and may be varied within the range of from about 1:1 to about 100:1. The temperature and pressure at which the reaction is effected falls within the ranges of between about 80° and 130° C., preferably between about 90° and about 120° C., under a pressure of from about 0 to about 50 mm Hg, preferably from about 0 to about 15 mm Hg. This reaction is carried out under anhydrous conditions preferably with constant removal of water by-product to maintain a favorable reaction equilibrium. The product of this reaction is recovered as a solid or as a solution in excess alcohol. Should it be desirable to isolate the compound, the solution can be distilled to remove alcohol; although for use as a catalyst in the vinylation reaction, the solution is employed without further processing.

The compounds of this invention find use in several applications. Specifically they are useful as chemical intermediates in reactions involving olefinic saturation and metalization of organic compounds. They also preform as catalysts in the vinylation of alkyleneoxylated alkene diols.

When used as a catalyst for the conversion of an alkyleneoxylated alkene diol to an alkyleneoxylated divinyl ether alkene, the salt catalyst can be formed in situ in the presence of MOY, using a high excess of the diol reactant. In this case, excess diol to MOY can be employed within the range of between about 100:1: and about 10:1, more frequently within the range of about 40:1 and about 15:1 and the mole ratio of diol to catalyst is within the range of from about 100:1 to about 10:1. Such a reaction is described by equation II combined with the following equation III.

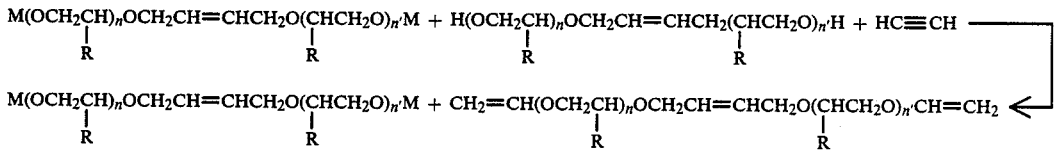   III.

In the above vinylation reaction, the catalyst is self regenerative in the presence of acetylene. The catalyst regeneration is described by the equilibrium equation:

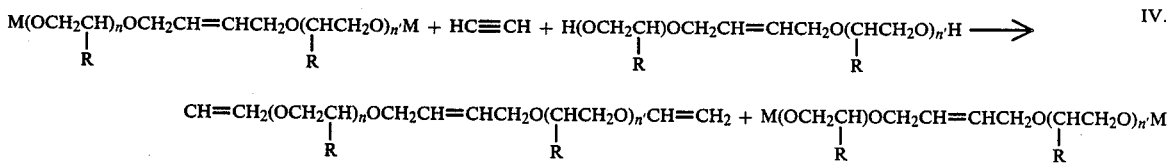   IV.

The vinylation reaction is carried out in a sealed container under anhydrous conditions while maintaining an excess of catalyst, for example a mole ratio of catalyst to diol of between about 1:100 and about 1:1. The operating conditions for the vinylation include a temperature of between about 130° and about 180° C., preferably between about 140° and 165° C. and a partial pressure of acetylene from about 50 to about 130 psig., preferably from about 80 to 100 psig.

The reaction is continued until cessation of acetylene absorption whereupon the alkyleneoxylated divinylether alkene product, if volatile, is recovered by vacuum distillation in greater than 90% purity. The recovery can be conveniently carried out by simple molecular distillation under less than 5 mm Hg pressure and at a product distillation temperature of between about 100° and about 200° C. Alternatively, any other convenient method can be employed for product recovery. For example, treatment with a 5% to 20% aqueous solution of sodium or potassium sulfate can be effected to extract the alkali metal salts into an aqueous layer followed by decolorizing the remaining product at a basic pH with charcoal or a similar decolorizing agent and then evaporating or heating to dryness.

The products of the vinylation reaction when used in a composition with a base resin form excellent protective coatings for metal and plastics. These coatings have high resistance to conventional commercial solvents and possess significantly increased flexibility as described in more detail in co-pending patent application FDN-1511, by the same inventors entitled "NON-DEGRADABLE PROTECTIVE COATINGS".

In the above reactions II through IV, the acetylene component is employed in 30% to 80% inert diluent such as propane, nitrogen or any other diluent gas which does not interfere with the reaction. This dilution of acetylene is recommended as a precaution against uncontrolled decomposition and/or explosion but is otherwise not essential to the operability of the reaction.

Having thus generally described the invention, reference is now had to the following Examples which illustrate preferred embodiments but which are not to be construed as limiting to the scope of the invention as more broadly described above and in the appended claims.

EXAMPLE 1

PREPARATION OF

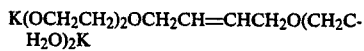

A sealed reactor is purged with nitrogen and the following mixture is introduced at a temperature of 110° C. under about 8 mm Hg pressure.

463 g. (2.5 moles) of diethoxylated 2-butene-1,4-diol; 20 g. of KOH

The reaction mixture was gently agitated for a period of about 20 minutes after which the product, diethoxylated 2-butene-1,4-diol potassium salt was formed in solution.

EXAMPLE 2

The process of Example 1 is repeated except that sodium methylate was substituted for potassium hydroxide. The diethoxylated 2-butene-1,4-diol sodium salt product is similarly produced.

EXAMPLE 3

The process of Example 1 is repeated except that non-alkyleneoxylated 2-butene-1,4-diol was substituted for the diethoxylated 2-butene-1,4-diol. The 2-butene-1,4-diol potassium salt is recovered in about 90% yield and purity.

EXAMPLE 4

Into an autoclave was introduced 480 grams of the product of Example 1, and a 50/50 propane-acetylene mixture to provide an acetylene partial pressure of 100 psig. The autoclave was sealed and heated to 160° C. for a period of 30 minutes after which the absorption of acetylene ceased. The autoclave was then cooled to room temperature, the contents discharged and the product was recovered by simple molecular distillation at about 1 mm Hg at a pot temperature of 150° C. in greater than 90% yield and purity. The product was identified by infrared and NMR spectroscopy.

Many modifications and substitutions in the above examples will become apparent from the foregoing description and disclosure; however these are to be included within the scope of this invention.

What is claimed is:

1. An alkali metal salt of an alkene having the formula

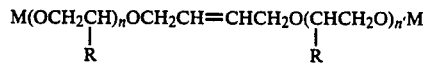

wherein M is an alkali metal; R is hydrogen or methyl and n and n' have a value of from 1 to 4.

2. The alkali metal salt of claim 1 wherein R is hydrogen.

* * * * *